US00PP26627P3

(12) United States Plant Patent
Danziger

(10) Patent No.: US PP26,627 P3
(45) Date of Patent: Apr. 19, 2016

(54) ***HEMEROCALLIS* PLANT NAMED 'DHEMORANGE'**

(50) Latin Name: ***Hemerocallis* hybrid**
Varietal Denomination: DHEMORANGE

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 220 days.

(21) Appl. No.: 13/999,327

(22) Filed: Feb. 10, 2014

(65) Prior Publication Data

US 2015/0230381 P1 Aug. 13, 2015

(51) Int. Cl.
*A01H 5/02* (2006.01)

(52) U.S. Cl.
USPC ..... Plt./312

(58) Field of Classification Search
USPC ..... Plt./263.1, 312
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Hemerocallis* cultivar named 'DHEMORANGE' is disclosed, characterized by very early blooming, very compact growth habit, continuous blooming, small easy to divide rhizomes and self-cleaning flowers. The new variety is a Hemerocallis, normally produced as an outdoor garden plant.

2 Drawing Sheets

Figure 1:
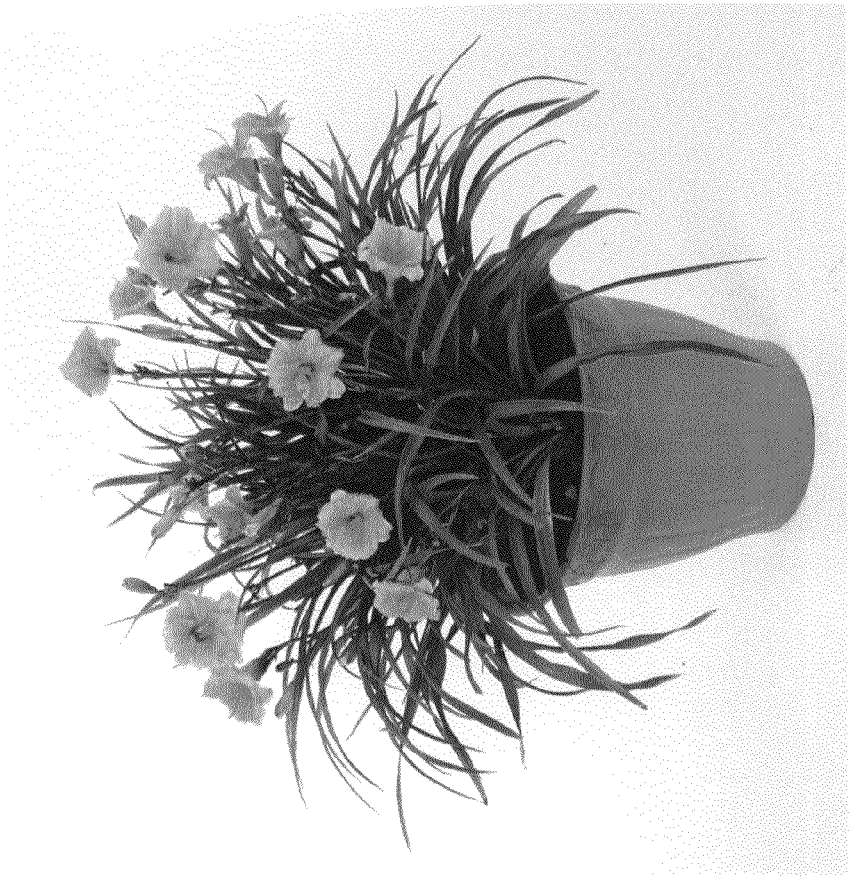

Latin name of the genus and species: *Hemerocallis* hybrid.
Variety denomination: 'DHEMORANGE'.

BACKGROUND OF THE INVENTION

The new *Hemerocallis* cultivar is a product of a planned breeding program conducted by the inventor, Gavriel Danziger, in Moshav Mishmar Hashiva, Israel. The objective of the breeding program was to produce new *Hemerocallis* varieties for ornamental commercial applications. The cross resulting in this new variety was made during the Spring of 2004.

The seed parent is the unpatented proprietary seedling variety referred to as *Hemerocallis* 'Hm-Z-20'. The pollen parent is the unpatented proprietary seedling variety referred to as *Hemerocallis* 'Hm-Z-10'. The new variety was discovered in the Spring of 2005 by the inventor in a group of seedlings resulting from the 2005 crossing, in a research greenhouse in Moshav Mishmar Hashiva, Israel.

Asexual reproduction of the new cultivar was first performed by tissue culture at a laboratory in Shedema, Israel in 2007 and has shown that the unique features of this cultivar are stable and reproduced true to type in 7 generations.

SUMMARY OF THE INVENTION

The cultivar 'DHEMORANGE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DHEMORANGE' These characteristics in combination distinguish 'DHEMORANGE' as a new and distinct *Hemerocallis* cultivar:

1. Very early flowering.
2. Very compact growth habit.
3. Continuous blooming.
4. Small easy to divide rhizomes.
5. Self-cleaning.
6. The unique combination of all the above characteristics.

Plants of the new cultivar 'DHEMORANGE' are similar to plants of the seed parent, *Hemerocallis* 'Hm-Z-20' in most horticultural characteristics, however, plants of the new cultivar 'DHEMORANGE' differ in the following ways;

1. More compact in form.
2. Earlier flowering.
3. More upright foliage.

Plants of the new cultivar 'DHEMORANGE' are similar to plants of the pollen parent; *Hemerocallis* 'Hm-Z-10' in most horticultural characteristics, however, plants of the new cultivar 'DHEMORANGE' differ in the following ways;

1. Earlier flowering.
2. Continuous flowering compared to pollen parent that re-blooms only once per year.
3. More compact in form.

COMMERCIAL COMPARISON

Plants of the new cultivar 'DHEMORANGE' are comparable to the well known, unpatented commercial variety *Hemerocallis* 'Stella d'Oro'. The two *Hemerocallis* varieties are similar in most horticultural characteristics; however, the new variety 'DHEMORANGE' differs in the following ways;

1. Earlier flowering.
2. More compact in form.
3. Orange flower color. The comparator has yellow colored flowers.
4. Easier to divide rhizomes.

Plants of the new cultivar 'DHEMORANGE' can also be compared to the unpatented commercial variety *Hemerocal-*

*lis* 'Pardon Me' These varieties are similar in most horticultural characteristics; however 'DHEMORANGE' differs in the following ways;

1. Earlier flowering.
2. More flower stems produced.
3. Continuous flowering. The comparator re-blooms once only.
4. Thinner stems.
5. Very compact growth habit. The comparator is of medium growth habit.

BRIEF DESCRIPTION OF THE PHOTOGRAPHS

The accompanying photograph in FIG. 1 illustrates in full color a typical plant of 'DHEMORANGE' grown in a greenhouse, in a 17 cm pot. Age of the plant photographed is approximately 1 year old.

Figure 2:
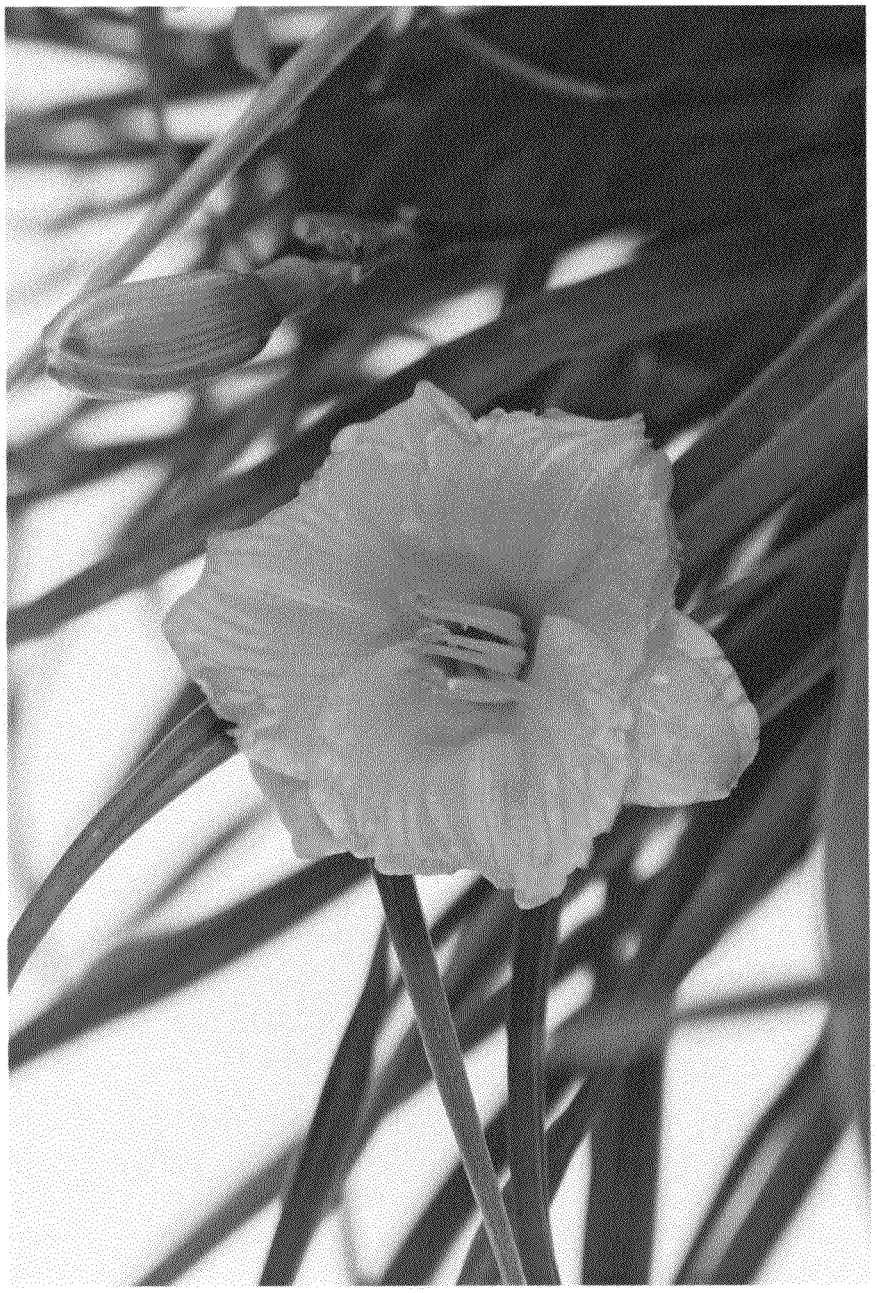

FIG. 2 illustrates in full color a close up of a typical bloom of 'DHEMORANGE'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DHEMORANGE' plants grown outdoors in Moshav Mishmar Hashiva, Israel. The growing temperature ranged from 20° C. to 35° C. during the day and from 17° C. to 23° C. during the night. General light conditions are bright, normal sunlight. Measurements and numerical values represent averages of typical plant types.

Botanical classification: *Hemerocallis* hybrid 'DHEMORANGE'.

PROPAGATION

Root description: Rhizomes. Thick, typically colored near Orange-White 159C.

Propagation method: Rhizome divisions or tissue culture.

PLANT

Age of plant described: Approximately 12 months.

Container size: 17 cm.

Growth habit: Dormant type.

Height: Approximately 26 cm to top of highest leaf. Approximately 36 cm to top of highest inflorescence.

Plant spread: Approximately 30 cm.

Growth rate: Flowers very early (like or somewhat earlier to Stella).

Branching characteristics: Non-branching, forms basal clumps.

FOLIAGE

Leaf:

*Arrangement.*—Upright.
*Average length.*—Approximately 25 cm.
*Average width.*—Approximately 1 cm.
*Shape of blade.*—Grass-like.
*Apex.*—Pointed.
*Base.*—Square.
*Sheathing.*—No.
*Margin.*—Smooth.
*Texture of top surface.*—Smooth.
*Texture of bottom surface.*—Smooth.
*Quantity of leaves per plant.*—Approximately 100.
*Color.*—Young foliage upper side: Near Green RHS 137B. Young foliage under side: Near Green RHS 137B. Mature foliage upper side: Near Green RHS 137A. Mature foliage under side: Near Green RHS 137B.
*Venation.*—Type: Linear. Venation color upper side: Near Green RHS 137B. Venation color under side: Near Green RHS 137B.

FLOWER

Natural flowering season: March-October.

Inflorescence type and habit: Single flowers occurring on a scape.

Flower longevity on plant: 24 hrs from fully opened.

Quantity of open flowers per plant at one time: 5-10.

Flowering scapes produced per year, on average: 20.

Inflorescence size:

*Height.*—Approximately 26 cm.
*Width.*—Approximately 8 cm.
*Flowers per inflorescence.*—Average: 15-25.

Individual corolla:

*Arrangement.*—
*Size.*—Length: Approximately 6.5 cm. Width: Approximately 5.5 cm at widest point.
*Tepals per corolla.*—1.
*Margin.*—Smooth.
*Shape.*—Bell shaped.
*Apex.*—Blunt.
*Texture.*—Smooth.

Color:

*Tepals.*—When opening: Outer surface: Near Orange RHS 24A. Inner surface: Near Orange RHS. 24B. Fully opened: Outer surface: Near Orange RHS 24A. Inner surface: Near Orange RHS 24B. Aging Flower color: Outer surface: Near Orange RHS 24B. Inner surface: Near Orange RHS 24B.

Bud:

*Shape.*—Elongated and oblong.
*Length.*—Approximately 3.5 cm.
*Diameter.*—Approximately 1 cm.
*Color.*—Near Green RHS 137B.

Scape:

*Length.*—Approximately 35 cm.
*Width.*—Approximately 0.4 cm.
*Angle.*—Upright.
*Strength.*—Very Strong.
*Color.*—Near Green RHS 137A.
*Scape foliage.*—Quantity: 2 pairs of leaves. Shape: Wide at base, pointed at end. Color: Near RHS Yellow-Green 144C. Length: 13 cm. Width: 1.5 cm at the base.

Peduncles:

*Quantity per scape.*—5.
*Length.*—Approximately 6-8 cm.
*Width.*—Approximately 0.5 cm.
*Aspect/angle.*—More acute than 45 degrees.
*Texture.*—Smooth.
*Color.*—Near Green RHS 137A.

REPRODUCTIVE ORGANS

Stamens:

*Number.*—Average 6.

*Filament length.*—Approximately 4 cm.

*Filament color.*—Near Orange RHS 24A.

*Anther length.*—0.4 cm.

*Anther color.*—Near Yellow-Orange RHS 23A.

*Anther shape.*—Symmetrical and oblong.

*Pollen.*—Viable.

Pistil:

*Number.*—1.

*Length.*—Approximately 5.5 cm.

*Style color.*—Near Orange RHS 29B.

*Stigma.*—Shape: Flat. Color: Near Orange RHS 29B.

*Ovary color.*—Near Green RHS 137B.

OTHER CHARACTERISTICS

Seeds and fruits: None observed to date.

Disease/pest resistance: Common to other *Hemerocallis* varieties.

Temperature tolerance: Tolerates temperatures from approximately below 0° C. to 35° C.

What is claimed is:

1. A new and distinct cultivar of *Hemerocallis* plant named 'DHEMORANGE' as herein illustrated and described.

* * * * *